United States Patent [19]

Kashihara et al.

[11] Patent Number: 4,920,187

[45] Date of Patent: Apr. 24, 1990

[54] PROCESS FOR PREPARING PARTICLES HAVING MONODISPERSE PARTICLE SIZE

[75] Inventors: Akio Kashihara, Hirakata; Chikayuki Otsuka, Kadoma; Katsukiyo Ishikawa, Kuze, all of Japan

[73] Assignee: Nippon Paint Co., Ltd., Osaka, Japan

[21] Appl. No.: 140,663

[22] Filed: Jan. 4, 1988

[30] Foreign Application Priority Data

Jan. 12, 1987 [JP] Japan .................................. 62-5283
Jan. 12, 1987 [JP] Japan .................................. 62-5284
Oct. 30, 1987 [JP] Japan ................................ 62-277067

[51] Int. Cl.$^5$ .............................................. C08F 2/00
[52] U.S. Cl. .................................... 526/193; 526/213;
526/214; 526/215; 526/216; 526/320;
526/318.4; 526/346; 526/312; 526/323.2;
526/329.2
[58] Field of Search ............... 526/193, 213, 214, 215,
526/216, 320, 318.4, 346, 312, 323.2, 329.2

[56] References Cited

U.S. PATENT DOCUMENTS

| | | | |
|---|---|---|---|
| 4,265,990 | 5/1981 | Stolka et al. ........................... | 430/96 |
| 4,282,304 | 8/1981 | Bayley ..................................... | 526/88 |
| 4,322,324 | 3/1982 | Mizuguchi et al. ................... | 528/294 |
| 4,379,872 | 4/1983 | Ishikua et al. ......................... | 524/723 |
| 4,379,873 | 4/1983 | Wilson .................................... | 524/435 |
| 4,390,649 | 6/1983 | Aharoni .................................. | 524/435 |
| 4,613,559 | 9/1986 | Ober et al. ............................. | 430/137 |

FOREIGN PATENT DOCUMENTS 2161170 1/1986 United Kingdom .

OTHER PUBLICATIONS

J61018966—1/27/86, "Production of Particles for Image Forming . . . Vinyl Monomer etc.".

*Primary Examiner*—Joseph L. Schofer
*Assistant Examiner*—N. Sarofin
*Attorney, Agent, or Firm*—Wenderoth, Lind & Ponack

[57] ABSTRACT

Disclosed is a process for preparing polymer particles having monodisperse particle size comprising:
adding a dispersion stabilizer, a polymerizable monomer and a polymerization initiator to an organic solvent to conduct polymerization, wherein said organic solvent has a solubility parameter (SP value) higher than that of the resultant polymer by at least 1.0 and said dispersion stabilizer is soluble in said organic solvent and has a free radical reactive group of $10^{-3}$ to 1 mmol/g; and
removing said organic solvent.

19 Claims, No Drawings

PROCESS FOR PREPARING PARTICLES HAVING MONODISPERSE PARTICLE SIZE

FIELD OF THE INVENTION

The present invention relates to resin particles suitable for column chromatography, clinical diagnosis and toners for electrography.

BACKGROUND OF THE INVENTION

Hitherto, polymer particles employed for many applications have been generally produced by emulsion polymerization, seed-emulsion polymerization or suspension polymerization. In emulsion polymerization, a particle size of the obtained polymer particles is of a submicron meter meter order. This does not meet the requirements of obtaining large particle sizes. In seed-emulsion polymerization, several steps are required to obtain a large particle size. This is a disadvantage in production cost and workability. In suspension polymerization, the obtained particles have a broad particle size distribution, which is not preferred for certain usages.

For improving the above defects, one or more vinyl monomers which are soluble in a hydrophilic organic solvent are polymerized in a solution of said hydrophilic organic solvent and a polymeric dispersant, to obtain a polymer which is not dissolved or swelled with the organic solvent (Japanese Patent Publication (unexamined) Nos. 18966.1986 and 228458/1986). The polymer particles thus obtained have a quite narrow particle size distribution, but which are still insufficient in certain utilities.

SUMMARY OF THE INVENTION

The present invention is to provide polymer particles which are easily produced and which have a monodisperse particle size. The polymer particles are prepared by adding a dispersion stabilizer, a polymerizable monomer and a polymerization initiator to an organic solvent to conduct polymerization, wherein said organic solvent has a solubility parameter (SP value) higher than that of the resultant polymer by at least 1.0 and said dispersion stabilizer is soluble in said organic solvent and has a free radical reactive group of $10^{-3}$ to 1 mmol/g; and then removing said organic solvent.

DETAILED DESCRIPTION OF THE INVENTION

According to the present invention, the dispersion stabilizer contains a free radical reactive group. A convention dispersion stabilizer, which does not have such a free radical reactive function group, physically attaches to a particle-forming polymer so as to easily leave the particles, thus often forming contaminations. For preventing the contaminations and making the particle size distribution more monodisperse, it is preferred that a dispersion stabilizer is block-copolymerized or graft-polymerized with a particle-forming polymer to form a blocked or grafted chain which has an excellent affinity to the particle-forming monomer. In other words, the dispersion stabilizer is copolymerized with the particle-forming monomer such as to be incorporated into the polymer matrix of the particles, through chemical bonding. Since the blocked or grafted chain has a high affinity for the monomer, the polymerization reaction further proceeds to obtain polymer particles having high monodisperse particle sizes. In order to incorporate the dispersion stabilizer, a free radical reactive group has to be introduced into the dispersion stabilizer. The free radical reactive group includes a polymerizable double bond or a mercapt group.

One class of the dispersion stabilizer employed in the present invention is a conventional dispersion stabilizer into which a polymerizable double bond is introduced. Examples of the conventional dispersion stabilizers are celluloses, such as hydroxyethyl cellulose, hydroxypropyl cellulose, cellulose acetate butylate, hydroxybutyl methyl cellulose, hydroxypropyl methyl cellulose, propionic acid cellulose and the like; polyvinyl alcohols, such as polyvinyl acetate, ethylene-vinyl alcohol copolymers, vinyl alcohol-vinyl acetate copolymers and the like; other polymers, such as polyvinyl pyrolidone, polyacrylic acid, polyvinyl methyl ether, acrylic resins, epoxy resins, styrene-acryl resins and the like; polycondensation polymers, such as polyester resins, polyethyleneimine and the like; zwitterion containing resins, such as zwitterion-containing polyesters or zwitterion-containing epoxy resins as described in Japanese Patent Publication (unexamined) Nos. 151727/1981 and 40522/1982; and the like.

In order to introduce the polymerizable vinyl group to the conventional dispersion stabilizer, all known methods can be employed. For example, where the conventional stabilizer has an active hydrogen, such as a hydroxyl group, a methylol group or an amino group, the introduction can be made by employing a compound having both a (meth)acryloyl group and an isocyanate group, such as methacryloyl isocyanate, isocyanatoethyl methacrylate and the like; a compound having both a (meth)acryloyl group and an alkoxysilane group, such as gamma-methacryloxypropyltrimethoxysilane and the like. If the conventional stabilizer has a carboxyl group, such as a polycarboxylic acid resin, a polyester resin or an acrylic resin, then a compound having both an oxirane ring or aziridine and a (meth)acryloyl group, such as glycidyl (meth)acrylate, aziridinylethyl (meth)acrylate and the like can be used for the introduction. It, of course, may be prepared by an addition reaction of a resin having an oxirane group or an aziridine group with an ethylenically unsaturated monomer, such as (meth)acrylic acid. Also, a product of an ester interchange reaction of cellulose acetate butylate with a mono- or di-alkyl maleate, and a polyester to which a maleic anhydride is added may be used as the dispersion stabilizer of the present invention.

Another class of the dispersion stabilizer is a conventional dispersion stabilizer into which a mercapt group is introduced. A method for introducing a mercapt group is that the conventional stabilizer having a hydroxyl group is condensed with mercaptcarboxylic acid or a mercaptalkyltrimethoxysilane, or that the conventional stabilizer having an ester bond is ester-interchanged with a mercaptcarboxylic acid. A mercapt group may also be introduced by polymerizing a polymerizable monomer (such as a vinyl ester, (meth)acrylic acid or a derivative therefrom, (meth)acrylonitrile, (meth)acrylamide, N-vinyl pyrolidone and the like) in the presence of a thiolic acid followed by saponification. Examples of thiolic acids are thiolglycolic acid, thiolmaleic acid, thiolsalicylic acid and the like.

A concentration of the free radical polymerizable double bond or the mercapt group in the dispersion stabilizer is within the range of $10^{-3}$ to 1 mmol/g, preferably $3 \times 10^{-3}$ to $5 \times 10^{-1}$ mmol/g based on dispersant solid contents. An amount of the dispersion stabilizer is not limited depending on a desired particle size, deformation degree and polymerization properties, but it may generally be from 0.5 to 20% by weight of a total amount of the polymerizable monomer. The dispersion stabilizer of the present invention may also contain both the double bond and the mercapt group. It may also be combined with the conventional dispersion stabilizer mentioned above. If necessary, the dispersion stabilizer which has a certain functional group may be employed to give electric charges to the obtained particles, although the electric charges can be given by the other components for the particles. Among the stabilizers are polyamino (meth)acrylate and polyethyeleneimine for imparting positive charges. For negative charges, polyacrylic acid or a polyester resin is preferred.

According to the present invention, an organic solvent having a solubility parameter more than that of the obtained resin particles by not less than 1, preferably 2 to 10 is employed. The "solubility parameter" herein is obtained from "Polymer Handbook" by H. Burrel, Wiley-Interscience, p. IV-337 to IV-348. The organic solvent to be employed includes ketones, such as acetone and cyclohexanone; dioxane, acetonitrile; dimethylformamide; ether alcohols, such as ethylene glycol monomethyl ether, ethylene glycol monoethyl ether, ethylene glycol monobutyl ether, propylene glycol monomethyl ether, propylene glycol monoethyl ether, propylene glycol monobutyl ether, diethylene glycol monomethyl ether, diethylene glycol monoethyl ether, diethylene glycol monobutyl ether, dipropylene glycol monomethyl ether, dipropylene glycol monoethyl ether; alcohols, such as methanol, ethanol, isopropanol, n-butanol, i-butanol, t-butanol, n-hexanol, cyclohexanol, ethylene glycol, propylene glycol, dipropylene glycol; and the like. Preferably, the solvent contains the alcohols and/or ether alcohol of not less than 50% by weight, more preferably not less than 80% by weight.

The polymerizable monomer of the present invention includes an alkyl (meth)acrylate, such as methyl acrylate, methyl methacrylate, ethyl acrylate, n-butyl acrylate, n-butyl methacrylate, 2-ethylhexyl acrylate and 2-ethylhexyl methacrylate; a hydroxyl group-containing monomer, such as 2-hydroxyethyl acrylate, hydroxypropyl acrylate, 2-hydroxyethyl methacrylate, hydroxypropyl methacrylate, hydroxybutyl acrylate, hydroxybutyl methacrylate, allyl alcohol and methallyl alcohol; polymerizable amides, such as acrylamide and methacrylamide; polymerizable nitriles, such as acrylonitrile, and methacrylonitrile; glycidyl (meth)acrylate; an aromatic vinyl compound, such as styrene and vinyl toluene; an alpha-olefin, such as ethylene and propylene; a vinyl compound, such as vinyl acetate and vinyl propionate; a diene compound, such as butadiene and isoprene; a carboxyl group-containing monomer, such as acrylic acid, methacrylic acid, crotonic acid, itaconic acid, maleic acid, fumaric acid, monobutyl itaconate, monobutyl maleate; a phosphoric acid group-containing monomer, such as acidphosphoxyethyl methacrylate, acidphosphoxypropyl methacrylate, 3-chloro-2-acidphosphoxypropyl methacrylate; a sulfonic acid group-containing monomer, such as 2-acrylamide-2-methylpropanesulfonic acid and 2-sulfoethyl methacrylate; a nitrogen-containing alkyl (meth)acrylate, such as dimethylaminoethyl acrylate and diethylaminoethyl methacrylate; a derivative therefrom, such as a reaction product of the hydroxyl group-containing monomer with an isocyanate compound and a reaction product of a carboxyl group-containing monomer with a glycidyl group-containing compound; and the like. For imparting negative charges, the carboxylic acid-containing monomer, phosphoric acid group-containing monomer and sulfonic acid group-containing monomer are preferred. For positive charges, the nitrogen containing monomer is preferred.

In addition to the above polymerizable monomer, a polyethylenic monomer may be employed to adjust a glass transition temperature of the polymer particles and a molecular weight. Examples of the polyethylenic monomers are ethylene glycol diacrylate, diethylene glycol dimethacrylate, triethylene glycol dimethacrylate, tetraethylene glycol dimethacrylate, 1,3-butylene glycol dimethacrylate, trimethylolpropane triacrylate, trimethylolpropane trimethacrylate, 1,4-butanediol diacrylate, neopentyl glycol diacrylate, 1,6-hexanediol diacrylate, pentaerythritol diacrylate, pentaerythritol triacrylate, pentaerythritol tetraacrylate, pentaerythritol dimethacrylate, pentaerythritol trimethacrylate, pentaerythritol tetramethacrylate, glycelol dimethacrylate, glycelol diacrylate, glycelol acryloxy dimethacrylate, 1,1,1-trishydroxymethylethane diacrylate, 1,1,1-trishydroxymethylethane triacrylate, 1,1,1-trishydroxymethylethane dimethacrylate, 1,1,1-trishydroxymethylethane triacrylate, 1,1,1-trishydroxymethylpropane diacrylate, 1,1,1-trishydroxymethylpropane triacrylate, 1,1,1-trishydroxymethylpropane dimethacrylate, 1,1,1-trishydroxymethylpropane trimethacrylate, triallyl cyanurate, triallyl isocyanurate, triallyl trimellitate, diallyl terephthalate, diallyl phthalate, divinylbenzene, diisopropenylbenzene or a mixture thereof. The polyethylenic monomer may be present in an amount of 0.2 to 50% by weight based on a total monomer amount. However, amounts of more than 50% by weight can be used. It is preferred that the polyethylenic monomer may be added at the end of polymerization process. This imparts a construction having a highly crosslinked shell and a core crosslinked not so much. The construction is very suitable for a toner particle.

Generally, polymerization can be carried out using polymerization initiator. The initiator is not limited, but includes a peroxide, such as benzoyl peroxide, di-t-butyl peroxide, cumen hydroperoxide or t-butylperoxy-2-ethylhexanoate; an azo compound, such as azobisisobutyronitrile, 2,2-azobis(2,4-dimethylvaleronitrile), 2,2'-azobis(4-methoxy-2,4-dimethylvaleronitrile or dimethyl-2,2'-azobisisobutyrate; and the like. A combination of the above initiator can be employed. An amount of the initiator is within the range of 0.1 to 10% by weight, preferably 0.2 to 7% by weight based on a total monomer amount. As already mentioned above, electric charges may be imparted by the initiator. For positive charges, the initiator includes an azo-amidine compound, such as 2,2'-azobis(2-amidinopropane)dihydrochloride, 2,2'-azobis(N,N'-dimethyleneisobutylamidine), 2,2'-azobis(N,N'-dimethyleneisobutylamidine)-dihydrochloride and the like. These are water soluble, so that it is employed in the form of an aqueous solution. An amount of this initiator is selected depending on a desired electric charge, but preferably within the range of 0.1 to 10% by weight based on a total monomer amount. For negative charge, an azo type carboxyl group-containing compound, such as 4,4'-azocis(4-cyanopentanoic acid) or persulfate, such as potassium persulfate or ammonium persulfate can be employed. These also are water-soluble, so that it can be used in the form of an aqueous solution. An amount of this initiator is selected depending on a desired electric charge, but preferably within the range of 0.1 to 10% by weight based on a total monomer amount. Especially, where the dispersion stabilizer having a mercapt group is employed, the initiator is preferably peroxides. In this instance, the block or graft copolymerization reaction of the dispersion stabilizer with the polymerizable monomer becomes rapid and smooth to obtain polymer particles having a uniform particle size because of an oxidation-reduction reaction between the mercapt group which has reducing function and the oxide which has oxidizing function.

During polymerization, a coloring agent can be formulated if necessary. The coloring agent includes an inorganic pigment, an organic pigment and a dye, for example, carbon black, Cinquacia red, disazo yellow, Carmine 6B, Direct Yellow, Direct Blue, phthalocyanine blue, quinacridone red, azo type metal complex green, azine compound, stearic acid modified azine compound, oleic acid modified azine compound (such as nigrosine), quaternary ammonium base compound, phthalocyanine green halide, flavanthrone yellow, perylene red, an azo compound having metal (such as copper, zinc, lead, iron and the like). The coloring agent may be present in an amount of 3 to 50% by weight based on a total monomer amount. It is preferred that the pigment is grafted by a polymer on the surface. A method for grafting is known to the art, for example Japanese Patent Publication (unexamined) No. 23133/1980. When the coloring agent is the organic dye, it is desired to be oil-soluble and to have high solubility to nonpolar solvent (such as a hydrocarbon solvent). It is more preferred that the dye has a free radical reactive double bond. Such a dye can be obtained by reacting a dye having an active hydrogen, such as a hydroxyl group, a thiol group and a primary or secondary amino group with an isocyanatoalkyl (meth)acrylate or (meth)acryloyl isocyanate. The dye is copolymerized with the polymer particle to uniformly disperse in it. This is very important for a color toner. In the case where the coloring agent is the pigment, it is preferred to use the pigment having a different electron charge from the particle forming polymer or the dispersion stabilizer, because the pigment is uniformly dispersed in the particle.

According to the present invention, an additive may be formulated in the particles. Examples of the additives are magnetic powder, such as magnetite and ferrite; polyethylene wax; polypropylene wax; a silicon compound; and the like. An amount of the additive is 0.1 to 5% by weight based on a total polymerizable monomer.

Conditions for polymerization are not specifically limited, but generally polymerization is conducted at a temperature of 40° to 150° C. in a nitrogen blanket.

According to the prevent invention, the spherical polymer particles having narrow particle size distribution in micron meter order can be obtained. The particles having a controlled surface electric charge can also be obtained in one step by the present invention. The polymerizable monomer used for forming the particles can be widely selected for adjusting desired properties, such as electric resistance, flowability, anticohesiveness and the like.

In the present invention, the dispersion stabilizer which has a free radical reactive group is participated in polymerization to introduce into the particle. A portion contributing to dispersion stability in the stabilizer remains on the surface. Accordingly, the dispersion stability exists on the particle surface, as similar to the conventional one, but it never leaves the surface. As a result substantially no contaminations nor materials bonded to the apparatus used are formed. In the case where the polymer particles are used for a toner for electrophotography, adhesion of the dispersion stabilizer to a photosensitive member and a carrier does not happen so as to improve picture quality. The coloring agent also is uniformly dispersed in the particle to form a distinctive image.

EXAMPLES

The present invention is illustrated by the following examples, which are not to be construed as limiting the present invention to their details.

REFERENCE EXAMPLE 1

Preparation of a dispersion stabilizer having a polymerizable vinyl group

A one liter separable flask equipped with a thermometer, a condenser, an oxygen introducing tube and a stirrer was charged with 70 parts by weight of hydroxypropyl cellulose and 560 parts by weight of dioxane and heated to 80° C. After identifying that the content was completely dissolved, it was cooled to 30° C. A solution dissolving 0.8 parts by weight of methacryloyl isocyanate with 70 parts by weight of ethylene glycol monomethyl ether acetate was then added dropwise while blowing oxygen gas into the flask, and kept at 30° C. for one hour. Next, dioxane in the mixture was completely replaced with 3-methoxybutanol using a vacuum apparatus to form a dispersion stabilizer solution having a nonvolatile content of 25%. It was identified by IR and NMR that the methacryloyl group remained and the isocyanate group disappeared. The reaction product had a iodine value of 2.58% (solid contents).

REFERENCE EXAMPLE 2

Preparation of a dispersion stabilizer having a polymerizable vinyl group

A one liter separable flask as described in Reference Example 1 was charged with 105 parts by weight of 3-methyl-3-methoxybutanol and heated to 100° C. A mixture of 268 parts by weight of t-butyl methacrylate, 178 parts by weight of n-butyl acrylate, 54 parts by weight of methacrylic acid and 3 parts by weight of azobisisobutyronitrile was added dropwise over 3 hours while blowing nitrogen gas in the flask, and kept at 100° C. for 30 minutes. Further, a solution dissolving 0.5 parts by weight of azobisisobutyronitrile in 20 parts by weight of 3-methyl-3-methoxybutanol was added dropwise for 30 minutes and kept at 100° C. for 2 hours. It was then heated to 110° C. while blowing oxygen gas and 6.3 parts by weight of triethylamine and a solution dissolving 0.75 parts by weight of hydroquinone monomethyl ether in 5 parts by weight of 3-methyl-3-methoxybutanol were added with stirring. Then, 7.1 parts by weight of diglycidyl methacrylate was added dropwise over 30 minutes and kept at 110° C. for 2 hours to obtain a resin varnish. The varnish had an acid value of 66 mg KOH/g (solid contents) and a number average molecular weight of 28,000. Also, the reaction product had a iodine value of 2.4 (solids). No oxirane group remained when identified by IR.

REFERENCE EXAMPLE 3

Preparation of a dispersion stabilizer having a polymerizable vinyl group

A one liter separable flask as described in Reference Example 1 was charged with 84 parts by weight of ethylene glycol monomethyl ether acetate and 21 parts by weight of dioxane and heated to 100° C. A mixture of 243 parts by weight of t-butyl methacrylate, 162 parts by weight of n-butyl acrylate, 90 parts by weight of N,N-dimethylaminoethyl methacrylate, 5 parts by weight of 2-hydroxyethyl methacrylate and 3 parts by weight of azobisisobutyronitrile was added dropwise over 3 hours while blowing nitrogen gas, and kept at 100° C. for 30 minutes. Further, a solution dissolving 0.5 parts by weight of azobisisobutyronitrile in 10 parts by weight of dioxane was added dropwise over 30 minutes and kept at 100° C. for 2 hours. It was cooled to 60° C. and a solution dissolving 4.2 parts by weight of methacryloyl isocyanate in 12 parts by weight of dioxane was added over 30 minutes while blowing oxygen gas and then kept at 60° C. for 30 minutes to terminate the reaction. When identified by IR and NMR, a methacryloyl group remained and no isocyanate group was seen.

REFERENCE EXAMPLE 4

Preparation of a dispersion stabilizer having a polymerizable vinyl group

A one liter separable flask as described in Reference Example 1 was charged with 200 parts by weight of Luviskol VA 73E (a vinyl pyrolidone-vinyl acetate copolymer available from BASF Company) and 600 parts by weight of methanol and adjusted to 40° C. with stirring. A solution dissolving 1.2 parts by weight of sodium hydroxide in 12 parts by weight of methanol was added and kept at 40° C. for 4 hours. The resultant mixture was purified by Soxhlet rinsing using methanol and then dried to obtain a saponified vinyl pyrolidone-vinyl acetate copolymer. The same flask was charged with 70 parts by weight of the saponified vinyl pyrolidone-vinyl acetate copolymer and 560 parts by weight of dioxane and heated to 80° C. to completely dissolve the content, followed by cooling to 30° C. A solution dissolving 0.27 parts by weight of methacryloyl isocyanate in 20 parts by weight of dioxane was added dropwise over 30 minutes while blowing oxygen gas, and kept at 30° C. for one hour. Dioxane was replaced with 2-methoxypropanol using a vacuum apparatus to obtain a solution having a nonvolatile content of 40%. When identified by IR and NMR, a methacryloyl group remained and no isocyanate group was seen. The obtained product had a iodine value of 0.9 (solid contents).

REFERENCE EXAMPLE 5

Preparation of a dispersion stabilizer having a mercapt group

A reaction vessel was charged with 2,400 parts by weight of vinyl acetate (hereinafter often referred to as "VAc"), 580 parts by weight of methanol and 0.02 parts by weight of thiolacetic acid and, after replacing inside of the vessel with nitrogen, the inside content of the reaction vessel was heated to 60° C. Then, 20 parts by weight of methanol containing 0.868 parts by weight of 2,2'-azobisisobutyronitrile was added to the reaction vessel. On the completion of addition, 60 parts by weight of a methanol solution containing 0.4 parts by weight of thiolacetic acid was added over 5 hours to obtain a polymerization degree of 61.3%. The reaction vessel, then, was cooled and the remaining vinyl acetate was removed together with methanol under a reduced pressure, during which methanol was continued to add, to form a methanol solution containing polyvinylacetate in a concentration of 49.5%. To a portion of the methanol solution was added another methanol solution containing NaOH in an amount sufficient to have a polyvinylacetate concentration of 35% by weight and a mol ratio of [NaOH]/[VAc] of 0.05, thus saponifying it at 40° C. to obtain a polyvinyl alcohol. The polyvinyl alcohol was purified by Soxhlet rinsing with methanol and a viscosity was measured at 30° C. to be $7.51 \times 10^{-3} \times P^{0.64}$, from which a polymerization degree calculated 1,200. A saponification degree was 58 mol %. The purified polyvinyl alcohol had a mercapt group in an amount of $7.22 \times 10^{-6}$ equivalent/g-polyvinyl alcohol, which was determined by a iodine oxidation process.

REFERENCE EXAMPLE 6

Preparation of a dispersion stabilizer having a mercapt group

A reaction vessel was charged with 64 parts by weight of hydroxypropyl cellulose, 700 parts by weight of dioxane and 0.025 part by weight of dibutyltin dilauryl and completely dissolved. After elevating a bulk temperature to 80° C., 35 parts by weight of a dioxane solution containing 5.02 parts by weight of gamma-mercaptopropyltrimethoxysilane was added dropwise for 30 minutes and kept at 80° C. for 4 hours. Dioxane was recovered under reduced pressure to obtain a hydroxypropyl cellulose solution in dioxane having a nonvolatile content of 20%. It had a mercapt content of $2.47 \times 10^{-4}$ equivalent/g, which was determined by titrating with iodine in water.

REFERENCE EXAMPLE 7

Preparation of a dispersion stabilizer having a mercapt group

A reaction vessel was charged with 100 parts by weight of acrylic acid, 190 parts by weight of n-butyl methacrylate and 6.1 parts by weight of thiolacetic acid and, after filling the inside of the vessel with nitrogen, a bulk temperature was elevated to 60° C. Then, a solution containing 0.3 parts by weight of 2,2'-azobisisobutyronitrile in 10 parts by weight of acrylic acid was added to polymerize. After 2 hours, a polymerization degree was 35.2%. On the completion of polymerization, it was poured into toluene to precipitate a polymer and unreacted acrylic acid and n-butyl methacrylate were removed by repeating precipitation and purification three times by using methanol and toluene. Next, 90 g of the obtained polymer was dissolved in 100 g of methanol and 50 ml of a 1N-methanol chloric acid solution was added to react at 40° C. for 5 hours. This was poured into acetone to separate the precipitated polymer, which was then dried followed by repeating precipitation and purification two times by using ice/acetone system to obtain an polyacrylic acid having a mercapt group at one terminal. A viscosity of the polyacrylic acid in 2 mol/liter of a NaOH aqueous solution at 30° C. was 0.2 dl/g. A content of the mercapt group was $9.65 \times 10^{-5}$ equivalent/g according to a titration with iodine in water.

REFERENCE EXAMPLE 8

Preparation of a dye having a free radical polymerizable double bond

In the same apparatus as Reference Example 1, 76 parts by weight of Solvent Red 24 and 450 parts by weight of tetrahydrofuran were dissolved at room temperature. A mixture of 22.2 parts by weight of methacryloyl isocyanate with 50 parts by weight of tetrahydrofuran was added dropwise for 30 minutes and kept at room temperature for 2 hours. Existence of a methacryloyl group and disappearance of an isocyanate group was identified by IR and NMR. Tetrahydrofuran was, then, removed under reduced pressure to obtain a red dye having a free radical polymerizable double bond.

REFERENCE EXAMPLE 9

Preparation of a dye having a free radical polymerizable double bond

A blue dye having a free radical polymerizable double bond was obtained as generally described in Reference Example 8, with the exception that 59.2 parts by weight of Disperse Blue 3 and 22.2 parts by weight of methacryloyl isocyanate were reacted at a temperature of water with ice.

EXAMPLE 1

Preparation of resin particles having monodisperse particle size

A one liter separable flask equipped with a thermometer, a condenser, a nitrogen introducing tube and a stirrer was charged with 28.8 parts by weight of the dispersion stabilizer of Reference Example 1, 384 parts by weight of isopropanol and 96 parts by weight of 2-methoxypropanol and heated to 70° C. After completely dissolving the content, a mixture containing 117.5 parts by weight of styrene, 2.5 parts by weight of 2-hydroxyethyl methacrylate and 3 parts by weight of azoisobutyrontrile was added and reacted at 70° C. for 18 hours to terminate the reaction. The reaction product was centrifuged to obtain white powder. When the powder was observed by an electron microscope, spherical polymer particles having a narrow particle size distribution of bout 5 micron meter were observed. The powder has a weight average particle size of 5.3 micron meter when measured by a coulter counter and a standard deviation of 0.23 micron meter.

EXAMPLE 2

Preparation of polymer particles having monodisperse particle size

The same one liter separable flask as Example 1 was charged with 30 parts by weight of the dispersion stabilizer of Reference Example 4, 405 parts by weight of ethanol and 27 parts by weight of butyl acetate and heated to 80° C. After completely dissolving the content, a mixture containing 125 parts by weight of styrene, 3 parts by weight of methacrylic acid, 22 parts by weight of m-diisopropenylbenzene and 3.5 parts by weight of benzoyl peroxide was added and reacted at 80° C. for 18 hours to terminate the reaction. The reaction product was centrifuged to obtain white powder. When the powder was observed by an electron microscope, spherical polymer particles having a narrow particle size distribution of bout 3.5 micron meter were observed. The powder has a weight average particle size of 3.5 micron meter when measured by a coulter counter and a standard deviation of 0.16 micron meter.

EXAMPLE 3

Preparation of polymer particles having monodisperse particle size

The same one liter separable flask as Example 1 was charged with 10 parts by weight of the dispersion stabilizer of Reference Example 5, 255 parts by weight of ethanol and 255 parts by weight of 2-methoxyethanol and heated to 75° C. After completely dissolving the content, a mixture containing 90 parts by weight of styrene, 0.9 parts by weight of benzoyl peroxide and 6.3 parts by weight of azobiscyclohexanenitrile was added and kept at 75° C. for 2 hours. It was then heated to 85° C. at which polymerization was continued for 18 hours to terminate the reaction. The reaction product was centrifuged to obtain white powder. When the powder was observed by an electron microscope, spherical polymer particles having a narrow particle size distribution of bout 8 micron meter were observed. The powder has a weight average particle size of 8.4 micron meter when measured by a coulter counter and a standard deviation of 0.32 micron meter.

EXAMPLE 4

Preparation of polymer particles having monodisperse particle size

The same one liter separable flask as Example 1 was charged with 18 parts by weight of the dispersion stabilizer of Reference Example 6, 460 parts by weight of t-butanol and 50 parts by weight of deionized water and heated to 60° C. After completely dissolving the content, a mixture containing 72 parts by weight of styrene, 12 parts by weight of 2-ethylhexyl acrylate, 4 parts by weight of dimethylaminoethyl methacrylate, 2 parts by weight of ethylene glycol dimethacrylate, 0.5 parts by weight of benzoyl peroxide and 1.5 parts by weight of bis(4-t-butylcyclohexyl)peroxy dicarbonate was added and kept at 60° C. for 2 hours. It was then heated to 80° C. at which polymerization was continued for 16 hours to terminate the reaction. The reaction product was centrifuged to obtain white powder. When the powder was observed by an electron microscope, spherical polymer particles having a narrow particle size distribution of bout 2 micron meter were observed. The powder has a weight average particle size of 1.8 micron meter when measured by a coulter counter and a standard deviation of 0.09 micron meter.

EXAMPLE 5

Preparation of color polymer particles

The same one liter separable flask as Example 1 was charged with 43 parts by weight of the dispersion stabilizer of Reference Example 1 and 492 parts by weight of ethanol and heated to 70° C. After completely dissolving the content, a mixture containing 74 parts by weight of styrene, 4 parts by weight of methacrylic acid, 18 parts by weight of n-butyl acrylate, 6 parts by weight of diisopropenylbenzene, 6 parts by weight of the dye of Reference Example 9 and 4.3 parts by weight of azobisisobutyronitrile was added and reacted at 70° C. for 24 hours to terminate the reaction. The reaction product was centrifuged to obtain blue powder. When the powder was observed by an electron microscope, spherical polymer particles having about 5 to 7 micron meter were observed. The powder has a weight average particle size of 6.4 micron meter when measured by a coulter counter and a standard deviation of 1.37 micron meter. The blue particles has a frictional charge of −21 microcoulomb/g. 30 parts by weight of the particles were mixed with 970 parts by weight of a ferrite carrier and employed in a copy machine (U-BIX-3,000 available from Konishiroku Photo Ind. Co. Ltd.) to copy a chart for test, thus obtaining reproducible and distinct blue image.

EXAMPLE 6

Preparation of color polymer particles

The same one liter separable flask as Example 1 was charged with 8.2 parts by weight of the dispersion stabilizer of Reference Example 5, 308 parts by weight of isopropyl alcohol and 102 parts by weight of deionized water and heated to 80° C. After completely dissolving the content, a mixture containing 76 parts by weight of styrene, 10.9 parts by weight of 2-ethylhexyl acrylate, 2.7 parts by weight of dimethylaminoethyl methacrylate, 0.4 parts by weight of divinylbenzene, 4.5 parts by weight of the dye of Reference Example 8, 1.8 parts by weight of benzoyl peroxide and 7.2 parts by weight of azobiscyclohexanenitrile was added and reacted at 80° C. for 16 hours to terminate the reaction. The reaction product was centrifuged to obtain red powder. When the powder was observed by an electron microscope, spherical polymer particles having about 6 to 8 micron meter were observed. The powder has a weight average particle size of 6.9 micron meter when measured by a coulter counter and a standard deviation of 1.06 micron meter. The red particles has a frictional charge of +18 microcoulomb/g. 30 parts by weight of the particles were mixed with 970 parts by weight of a ferrite carrier and employed in a copy machine (SP-8100 available from Sharp Kabushiki K.K.) to copy a chart for test, thus obtaining reproducible and distinct red image.

EXAMPLE 7

Preparation of color polymer particles

The same one liter separable flask as Example 1 was charged with 4 parts by weight of the resin varnish of Reference Example 2, 576 parts by weight of ethyl alcohol and 72 parts by weight of 2-methoxypropanol and heated to 70° C. 12 parts by weight of Firstgen Blue 5,490 (copper phthalocyanine available from Dainippon Inc and Chemicals Inc.) was preliminary ground using a table SG mill with a mixture of 72 parts by weight of 2-methoxypropanol and 11 parts by weight of the resin varnish of Reference Example 2 and then 60 parts by weight of styrene, 17 parts by weight of n-butyl methacrylate and 3 parts by weight of 1,6-hexanediol dimethacrylate were added to form a pigment suspension. An initiator solution was prepared by dissolving 1.6 parts by weight of azobisisocyanovaleric acid in 16 parts by weight of deionized water, which was added to the flask and mixed for 10 minutes. The pigment suspension was added dropwise to the flask and mixed for one hour. On the completion of addition, it was allowed to stand for one hour and a solution of 0.8 parts by weight of azobisisocyanovaleric acid in 8 parts by weight of deionized water was added to form a mixture. The mixture was heated to 80° C. and left for 5 hours to terminate the reaction. The resultant dispersion was dried using a spray drier to remove the solvent and subjected to a labo jet mill to obtain a blue powder.

When the powder was observed by an electron microscope, spherical polymer particles having about 6 to 8 micron meter were observed. A content of the particles having a distortion degree of not more than 4/5 was about 75%. Phthalocyanine particles are scarcely seen when observed at 40,000 times. The powder has a weight average particle size of 12 micron meter when measured by a coulter counter and a standard deviation of 2.4 micron meter. The powder was dispersed in methanol and rinsed repeatedly. It was then centrifuged to separate the powder. The powder was again dispersed in water followed by rinsing and centrifuged. No polymer compounds were not existent in the separated methanol and water. The particles has a frictional charge of −29 microcoulomb/g. By employing a copy machine (U-BIX-3000), a copy test was conducted as generally described in Example 5 to obtain reproducible and distinct red image.

EXAMPLE 8

Preparation of color polymer particles

The same one liter separable flask as Example 1 was charged with 4 parts by weight of the resin of Reference Example 7, 272 parts by weight of t-butanol and 366 parts by weight of 3-methyl-3-methoxybutanol and heated to 80° C. Separately, 18 parts by weight of Lubicron Red 400RG (available from Tohsoh Inc.) was preliminary ground using a table SG mill with a mixture of 12 parts by weight of t-butanol and 8 parts by weight of the resin of Reference Example 7 and then 68 parts by weight of styrene, 22 parts by weight of n-butyl acrylate and 3.6 parts by weight of benzoyl peroxide were added to form a pigment suspension. The pigment suspension was added dropwise to flask over 6 hours and kept at 80° C. for 12 hours. A mixture of 23 parts by weight of styrene, 6 parts by weight of n-butyl acrylate, 2 parts by weight of methacrylic acid, 0.6 parts by weight of divinylbenzene and 1 part by weight of azobisisobutyronitrile was added dropwise over one hour and a solution of 30 parts by weight of t-butanol and 1 part by weight of azobisisobutyronitrile was added dropwise over 2 hours. It wa left for 4 hours to terminate the reaction.

The resultant dispersion was dried using a spray drier to remove the solvent and subjected to a labo jet mill to obtain a red powder. When the powder was observed by an electron microscope, spherical polymer particles having 9 to 16 micron meter were observed. A content of the particles having a distortion degree of not more than 4/5 was about 80%. Lubicron Red 400 RG particles are scarcely seen when observed at 40,000 times. The powder has a weight average particle size of 13 micron meter when measured by a coulter counter and a standard deviation of 2.2 micron meter. The powder was dispersed in methanol and rinsed repeatedly. It was then centrifuged to separate the powder. The powder was again dispersed in water followed by rinsing and centrifuged. No polymer compounds were not existent in the separated methanol and water. The particles has a frictional charge of −46 microcoulomb/g. By employing a copy machine (U-BIX-3000), a copy test was conducted as generally described in Example 5 to obtain reproducible and distinct red image.

EXAMPLE 9

Preparation of color polymer particles

The same one liter separable flask as Example 1 was charged with 32 parts by weight of the dispersion stabilizer of Reference Example 1, 440 parts by weight of isopropanol, 110 parts by weight of 2-ethoxyethanol and 8 parts by weight of Firstgen Blue NK (available from Dainippon Ink and Chemicals Ltd.) and heated to 70° C. A mixture of 51 parts by weight of styrene, 13 parts by weight of 2-ethylhexyl acrylate, 6 parts by weight of methacrylic acid and 1.5 parts by weight of azobisisobutyronitrile was added and mixed for 2 hours. Then, a mixture of 21 parts by weight of styrene, 4.1 parts by weight of 2-ethylhexyl acrylate, 2.5 parts by weight of methacrylic acid, 2.4 parts by weight of diisopropenylbenzene and 0.6 parts by weight of benzoyl peroxide was added dropwise over 30 minutes and heated to 80° C. to continue reaction for 15 hours. The resultant dispersion was dried using a spray drier to remove the solvent and subjected to a labo jet mill to obtain a blue powder. When the powder was observed by an electron microscope, spherical polymer particles having 8 to 13 micron meter were observed. A content of the particles having a distortion degree of not more than 4/5 was about 85%. Firstgen Blue are scarcely seen when observed at 40,000 times. The powder has a weight average particle size of 11 micron meter when measured by a coulter counter and a standard deviation of 3.3 micron meter. The powder was dispersed in methanol and rinsed repeatedly. It was then centrifuged to separate the powder. The powder was again dispersed in water followed by rinsing and centrifuged. No polymer compounds were not existent in the separated methanol and water. The particles has a frictional charge of −34 microcoulomb/g. By employing a copy machine (U-BIX-3000), a copy test was conducted as generally described in Example 5 to obtain reproducible and distinct blue image.

EXAMPLE 10

Preparation of color polymer particles

The same one liter separable flask as Example 1 was charged with 582 parts by weight of isopropanol and heated to 80° C. Separately, 8 parts by weight of Monark (carbon black available from Cabot Corporation) was preliminary ground using a table SG mill with a mixture of 9.7 parts by weight of isopropanol and 16.3 parts by weight of the resin varnish of Reference Example 3 and then added to the flask. A mixture of 120 parts by weight of styrene and 15 parts by weight of n-butyl acrylate, and a 20% aqueous solution of azobis(2-amidinopropane)dihydrochloride were respectively added dropwise over 1 hour and then left at 80° C. for 18 hours. The resultant dispersion was dried using a spray drier to remove the solvent and subjected to a labo jet mill to obtain a black powder. When the powder was observed by an electron microscope, spherical polymer particles having 4 to 8 micron meter were observed. A content of the particles having a distortion degree of not more than 4/5 was 90%. Carbon black particles are scarcely seen when observed at 40,000 times. The powder has a weight average particle size of 6.3 micron meter when measured by a coulter counter and a standard deviation of 1.0 micron meter. The powder was dispersed in methanol and rinsed repeatedly. It was then centrifuged to separate the powder. The powder was again dispersed in water followed by rinsing and centrifuged. No polymer compounds were not existent in the separated methanol and water. The particles has a frictional charge of +24 microcoulomb/g. By employing a copy machine (SP-8100), a copy test was conducted as generally described in Example 5 to obtain reproducible and distinct black image.

EXAMPLE 11

Preparation of color polymer particles

The same one liter separable flask as Example 1 was charged with 500 parts by weight of ethanol, 57 parts by weight of diethylene glycol monomethyl ether acetate and 10 parts by weight of the dispersion stabilizer of Reference Example 5 and heated to 80° C. Separately, 8 parts by weight of Graft Carbon M-3 (available from Mitsubishi Chemical Industry Ltd.) was preliminary ground using a table SG mill with a mixture of 12 parts by weight of ethanol, 0.4 parts by weight of Solsperse 12000 (a dispersant available from ICI Company) and 1.2 parts by weight of Solsperse 20000 and then added to the flask. A mixture of 66.9 parts by weight of styrene, 16.7 parts by weight of 2-ethylhexyl acrylate, 10.4 parts by weight of dimethylaminoethyl methacrylate, 2 parts by weight of benzoyl peroxide and 3 parts by weight of azobiscyclohexanenitrile dimethacrylate was added and left at 80° C. for 10 hours. A mixture of 21 parts by weight of styrene, 3.6 parts by weight of 2-ethylhexyl acrylate, 4.4 parts by weight of dimethylaminoethyl methacrylate and 2 parts by weight of m-diisopropenylbenzene was added dropwise over 2 hours and kept for 10 hours to terminate the reaction.

The resultant dispersion was dried using a spray drier to remove the solvent and subjected to a labo jet mill to obtain a black powder. When the powder was observed by an electron microscope, spherical polymer particles having 5 to 8 micron meter were observed. A content of the particles having a distortion degree of not more than 4/5 was about 95%. Carbon black particles are scarcely seen when observed at 40,000 times. The powder has a weight average particle size of 6.9 micron meter when measured by a coulter counter and a standard deviation of 0.9 micron meter. The powder was dispersed in methanol and rinsed repeatedly. It was then centrifuged to separate the powder. The powder was again dispersed in water followed by rinsing and centrifuged. No polymer compounds were not existent in the separated methanol and water. The particles has a frictional charge of +36 microcoulomb/g. By employing a copy machine (SP-8100), a copy test was conducted as generally described in Example 5 to obtain reproducible and distinct red image.

What is claimed is:

1. A process for preparing polymer particles having a narrow particle size distribution range comprising:
    adding a dispersion stabilizer, a polymerizable monomer and a polymerization initiator to an organic solvent to conduct polymerization such as to produce polymer particles dispersed in the organic solvent, wherein said organic solvent has a solubility parameter (SP value) higher than that of the resultant polymer by at least 1.0 and wherein said dispersion stabilizer is soluble in said organic solvent and has a free radical reactive group at a concentration within the range of $10^{-3}$ to 1 mmol/g based on the dispersant solid contents and which dispersion stabilizer functions by producing a stable dispersion of the polymer in said organic solvent said free radical reactive groups including a polymerizable double bond or a thiol group, which free radical groups react with said polymerizable monomer such as to chemically bond the dispersion stabilizer onto the polymer particles thus-produced; and removing said organic solvent to produce the polymer particles.

2. The process according to claim 1 wherein said free radical reactive group is a free radical polymerizable double bond.

3. The process according to claim 1 wherein said free radical reactive group is a thiol group.

4. The process according to claim 1 wherein to said polymerization initiator is an organic peroxide.

5. The process according to claim 1 wherein said polymerizable monomer contains 0.2 to 50% by weight of a polyethylenically monomer based on the total amount of said monomer.

6. The process according to claim 1 wherein to said organic solvent is added a coloring agent.

7. The process according to claim 6 wherein said coloring agent is dye having a free radical polymerizable double bond.

8. The process according to claim 7 wherein said dye having a free radical polymerizable double bond is prepared by an addition reaction of a dye having an active hydrogen with a methacryloyl isocyanate.

9. The process according to claim 6 wherein said polymerizable monomer contains an amino group-containing polymerizable monomer.

10. The process according to claim 6 wherein said polymerization initiator is an azo amidine compound.

11. The process according to claim 6 wherein said dispersion stabilizer has an amino group.

12. The process according to anyone of claims 9 to 11 wherein said coloring agent is an acidic pigment or dye.

13. The process according to claim 6 wherein said polymerizable monomer has a carboxyl group, a phosphoric acid group, a sulfonic acid group, a persulfate group or a halogen atom.

14. The process according to claim 6 wherein said polymerization initiator is an azo carboxyl compound.

15. The process according to claim 6 wherein said dispersion stabilizer has a carboxyl group, a phosphoric acid group, a sulfonic acid group or a sulfuric acid group.

16. The process according to anyone of claims 13 to 15 wherein said coloring agent is a basic pigment or dye.

17. The process of claim 1 wherein the dispersion stabilizer is added in sufficient amounts to produce polymer particles of a substantially uniform size such that the particles have a narrow particle size range distribution.

18. The process of claim 17 wherein the dispersion stabilizer is added in an amount of 0.5 to 20% by weight, based on the total amount of the polymerizable monomer.

19. The process of claim 18 wherein the polymerization initiator is present in an amount of 0.1 to 10% by weight, based on the total monomer content.

* * * * *